United States Patent [19]
Jonkman

[11] Patent Number: 5,769,828
[45] Date of Patent: Jun. 23, 1998

[54] TWO-STAGE VENOUS CANNULA WITH EXPANDABLE REINFORCING MEMBER

[75] Inventor: Kenneth R. Jonkman, Grand Rapids, Mich.

[73] Assignee: Medtronic, Inc., Minneapolis, Minn.

[21] Appl. No.: 663,563

[22] Filed: Jun. 13, 1996

[51] Int. Cl.$^6$ ............................................. A61M 25/00
[52] U.S. Cl. ............................ 604/280; 604/282; 604/53
[58] Field of Search .................................. 604/280, 282, 604/27, 35, 43, 52, 53, 264

[56] References Cited

U.S. PATENT DOCUMENTS

| | | | |
|---|---|---|---|
| 4,129,129 | 12/1978 | Amrine | 128/214 R |
| 4,639,252 | 1/1987 | Kelly et al. | 604/282 |
| 5,643,226 | 7/1997 | Cosgrove et al. | 604/280 X |

Primary Examiner—John D. Yasko
Attorney, Agent, or Firm—Harold R. Patton; Peter Forrest

[57] ABSTRACT

A two-staged venous cannula is disclosed. The cannula includes an expandable reinforcing member around the atrial basket that prevents the cannula from kinking or collapsing in the area where the reinforcing member is applied. The reinforcing member preferably consists of an even number of rigid discrete beams of the same length equally spaced about the circumference of a cylinder. In an alternate embodiment, the beams may be equally spaced on the surface of a cone. Alternate spaces between the beams are formed. The alternate spaces between the beams are equally spaced around the circumference of the cannula. The alternate spaces between the beams remain equally spaced around the circumference of the cannula as the reinforcing member is expanded over a larger diameter. This design for the reinforcing member provides space between the beams where holes of the preferred shape, size and orientation can be placed through the cannula without requiring cutting through the material of the reinforcing member.

38 Claims, 5 Drawing Sheets

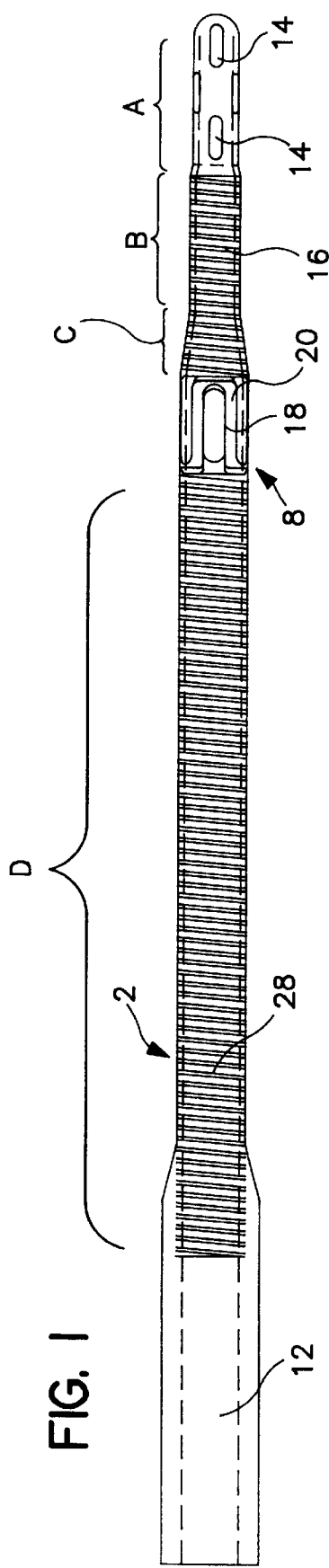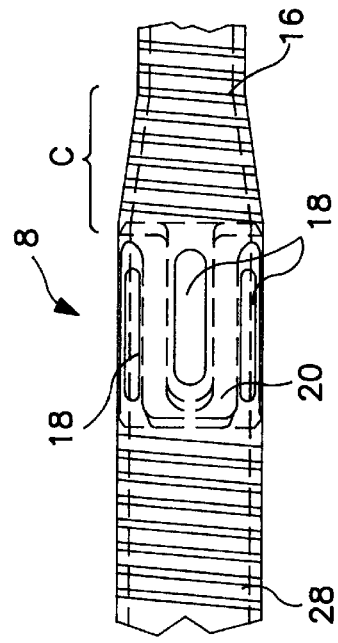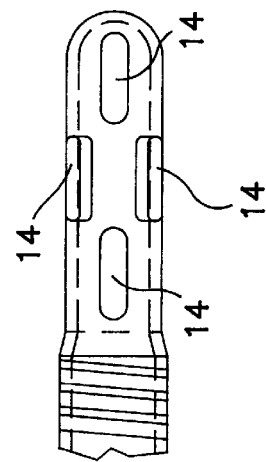

TWO-STAGE VENOUS CANNULA WITH EXPANDABLE REINFORCING MEMBER

BACKGROUND OF THE INVENTION

1. Field of the Invention

This invention relates to an invention for draining blood from the right atrium of a heart and more specifically relates to a two stage venous cannula with an expandable reinforcing member to prevent the cannula from kinking or collapsing in the perforated area where the reinforcing member is applied.

2. Description of Related Art

During cardiac surgery, it is often desirable to maintain circulation of blood through a patient's body. This is often done by connecting a patient to an extra-corporeal system that adds oxygen to and removes carbon dioxide from the blood, heats or cools the blood and provides impetus to the blood to cause the blood to circulate through the patient's vascular system.

It is necessary to connect the patient to the extra-corporeal circuit. This is usually done by inserting cannula into the patient's venous system near or in the heart to remove blood from the patient and direct it to the extra-corporeal circuit. After the blood has passed through the extra-corporeal circuit, the blood in infused into the patient's arterial system near the heart.

In practice, to remove the patient's venous blood, it is preferable to use a single two-stage venous cannula to simultaneously drain the right atrium and superior vena cava through an atrial basket while the inferior vena cava is drained through the distal tip segment. The distal tip is usually bullet-shaped to facilitate insertion.

The two-stage venous cannula was introduced by Sarns, Inc. of Ann Arbor, Mich. to the cardiac surgery market in the late 1970's as an alternative to bi-caval venous cannulation on procedures for coronary artery by-pass grafts (CABG). U.S. Pat. No. 4,129,129, issued to Bruce A. Amrine on Dec. 12, 1978 discloses such a two-stage venous catheter.

U.S. Pat. No. 4,639,252 issued to Michael N. Kelly, et al. on Jan. 27, 1987 discloses a two-stage venous catheter with a reinforcing member around the blood drainage openings. The reinforcing member is made of a harder stiffer material than the rest of the catheter. The reinforcing member is preferably incorporated in the body of the catheter. The reinforcing member is wrapped in strips around an initial layer of plastisol. A second layer of plastisol is applied to the reinforcing member. Holes are then punched through the reinforcing member and through the layers of plastisol.

SUMMARY OF THE INVENTION

A two-staged venous cannula is disclosed. The cannula has a bullet-shaped tip having side access ports to allow blood to enter the interior of the cannula through the side access ports. An enlarged atrial basket is placed a distance from the tip. The atrial basket has a series of slotted openings allowing blood to flow through the slotted openings into the interior of the cannula.

The cannula includes an expandable reinforcing member around the atrial basket that prevents the cannula from kinking or collapsing in the area where the reinforcing member is applied. The reinforcing member preferably consists of an even number of discrete beams of the same length equally spaced about the circumference of a cylinder. In an alternate embodiment, the beams may be equally spaced on the surface of a cone.

In either embodiment, one end of each beam is attached to the clockwise adjacent beam and the other end of the beam is attached to the counterclockwise adjacent beam thereby forming a device that is cylindrical or conical in shape. Alternate spaces between the beams are created that are open on opposite ends. The alternate space, between the beams are preferably equally spaced around the circumference of the cylinder or the surface of a cone.

A key feature of this reinforcing member is the tendency of the alternate spaces between the beams to remain equally spaced around the circumference of a cylinder car surface of a cone as the reinforcing member is expanded over a larger diameter.

Another advantage of this design for the reinforcing member is that it provides space between the reinforcing member material where holes of the preferred shape, size and orientation can be placed through the cannula without requiring cutting through the relatively rigid material of the reinforcing member. This results in cleaner holes with fewer burrs and in longer punch life.

A further advantage of this design for the reinforcing member is that it provides a combination of expandability and rigidity due to the shape of the reinforcing member, that is, long slot-like spaces between the beams with alternating open ends.

The two-stage venous cannula is made of a flexible material for most of its length so that the cannula may be easily inserted into the patient's heart through the superior vena cave. However, around the slotted openings at the atrial basket where blood flows into the cannula, the reinforcing member prevents kinking or collapsing of the cannula during normal use.

It is therefore an object of the present invention to provide a two-stage venous cannula that is flexible enough to be easily inserted into a patient's heart through the atrial appendage.

It is another object of the invention to provide a two-stage venous cannula that resists kinking and collapse during normal use, especially around the blood inlets to the cannula at the atrial basket.

It is a further object of the invention to provide a two-stage venous cannula with a reinforcing member that maintains the equal spacing between the beams of the member as the reinforcing member is expanded over a larger diameter.

It is another object of the invention to provide a two-stage venous cannula with a reinforcing member with spaces between the material of the reinforcing member so that holes of the preferred shape, size and orientation can be placed through the cannula without requiring cutting through the material of the reinforcing member.

It is another object of the invention to provide a two-stage venous cannula made by a process that results in cleaner holes for the blood to enter the cannula through with fewer burrs and that results in longer punch life for the machine punching the holes in the cannula.

These and other objects and advantages of the invention will be clear from the description contained herein and more particularly with reference to the following detailed description of the invention with its accompanying reference to the attached drawings. Throughout the description, like elements are referred to with like reference numbers.

BRIEF DESCRIPTION OF THE DRAWINGS

FIG. 1 is a side elevational view of the two-staged venous cannula of the present invention.

FIG. 2 is a close-up side elevational view of the distal bullet-shaped tip of the cannula of FIG. 1.

FIG. 3 is a close-up side elevational view of the atrial basket area of the cannula of FIG. 1.

DETAILED DESCRIPTION OF THE INVENTION

Figure 4A:
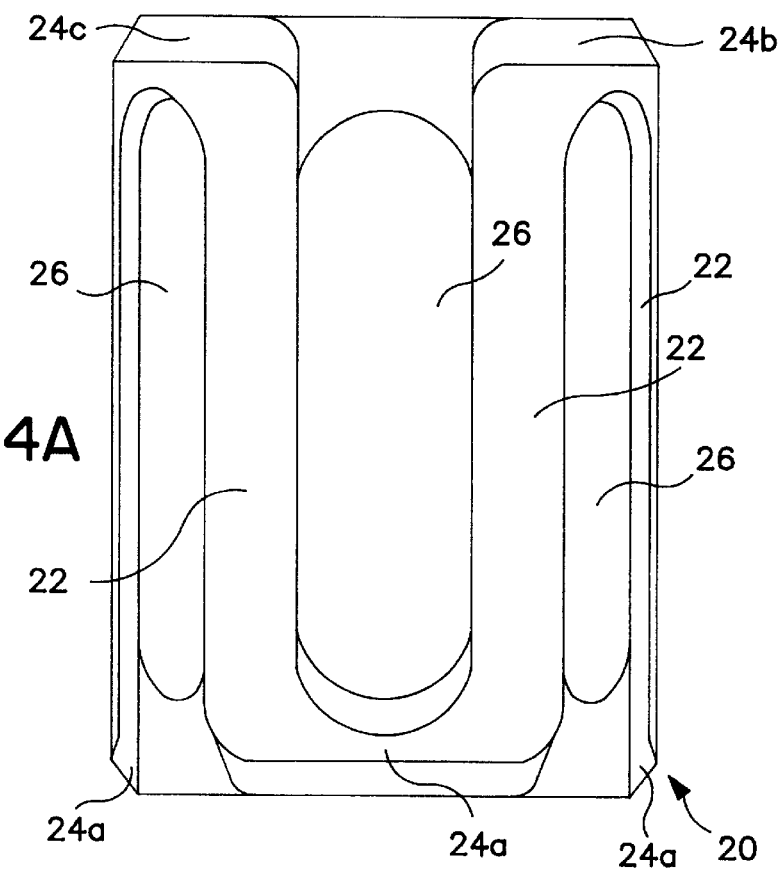
FIG. 4 is a side elevational view of the reinforcing member of the cannula of FIG. 1.

FIG. 1 shows a two-staged venous cannula according to the present invention, generally labeled 2. Cannula 2 has a distal end 4 and a proximal end 6 and an atrial basket area 8. Cannula 2 is comprised primarily of elongated tubular body 10 having, an interior lumen 12 shown in phantom in FIG. 1. Interior lumen 12 extends from the proximal end 6 to the distal end 4 of cannula 2. Interior lumen 12 is open at the proximal end 6 to allow cannula 2 to be connected to an extra-corporeal cardiac bypass system. However, interior lumen 12 is essentially closed at distal end 4.

A series of holes 14, shown in detail in FIG. 2, are formed near the distal end 4 of cannula 2. The area of distal end 4 containing holes 14 is shown in FIG. 1 generally labeled "A". Holes 14 extend from the outside of the distal end 4 to the lumen 12 of cannula 2. In use, distal end 4 is preferably placed through the heart into the inferior vena cava slightly above the hepatic vein. Holes 14 provide openings to allow blood to pass from the inferior vena cava to the lumen 12. The blood in lumen 12 then flows through cannula 2 to exit cannula 2 through proximal end 6 to ultimately enter an extra-corporeal cardiac bypass system.

In the preferred embodiment, holes 14 are elongated and have the axis of elongation aligned with lines that are parallel to the elongated axis of cannula 2. In addition, holes 14 are preferable equally spaced around the outer surface of cannula 2 at distal end 4. Holes 14 may also be placed in several rows, each row spaced a different distance from the ultimate distal end of distal end 4.

Where multiple holes 14 are provided, it may be preferable to alternate holes 14 in spacing around the outer surface of distal end 4 so that holes 14 in one row are offset from the holes 14 in another row. This arrangement forms a more rigid distal end 4.

Cannula 2 in the area of A preferably has a narrower outer diameter than the rest of cannula 2 to allow distal tip 4 to be placed in the inferior vena cava. In the preferred embodiment, the outer diameter of cannula 2 in area A is about 0.420 inches. In addition, the ultimate distal end of distal end 4 is preferable formed in a rounded or "bullet-shaped" configuration as shown in FIG. 2. This allows for easier insertion of cannula 2 into the patient's inferior vena cava. Cannula 2 in the inferior vena cava prevents the inferior vena cava from kinking while the heart is manipulated during cardiac surgery.

An area of cannula 2 generally labeled "B" in FIG. 1 extends proximally from the proximal end of area A. In the preferred embodiment, a spring 16 is added to the cannula 2 in area B to make cannula 2 in area B more rigid and kink resistant. Spring 16 is preferably a helical wire having a diameter of about 0.015 inch. Spring 16 is preferably integrally formed in cannula 2 at area B as described hereafter.

Because spring 16 is added to area B, the outer diameter of cannula 2 in area, B is slightly larger than the outer diameter of cannula 2 in area A. In the preferred embodiment, this outer diameter of cannula 2 in area B is about 0.450 inches. In addition, the combined length of areas A and B should be such that when the atrial basket 8 is in the center of the right atrium, the distal tip 4 will be in the inferior vena cava slightly above the hepatic vein.

Although in the preferred embodiment, the outer diameter of cannula 2 in area B is slightly larger than the outer diameter of cannula 2 in area A, this is not required to be so. It is within the scope of the invention that the outer diameter of cannula 2 in area B may be equal to or less than the outer diameter of cannula 2 in area A. Further, area B may be made more rigid and kink resistant by means other than spring 16. These means include, but are not limited to adding a stiffening layer to cannula 2 in area B and adding cross-linking agents to the plastisol that forms area B as will be described hereafter.

An area generally labeled "D" extends proximally from the proximal end of atrial basket 8. The outer diameter of cannula 2 in area D is preferably larger than the outer diameter of cannula 2 in area B. In the preferred embodiment, this larger diameter of cannula 2 in area D is about equal to about 0.600 inches.

A transition area from area B to the atrial basket 8 is shown in FIG. 1 generally labeled "C." Area C extends proximally from the proximal end of area B to the distal end of the atrial basket 8. Cannula 2 in transition area C expands from the outer diameter of cannula 2 at the proximal end of area B to the enlarged diameter of cannula 2 at the atrial basket 8. The purpose of transition area C is to allow cannula 2 to acquire a diameter in areas A and B that allows the distal end 4 to move into the inferior vena cava. The length of transition area C is preferably about 0.600 inches.

At atrial basket 8, holes 18 are placed through cannula 2 allowing blood outside of cannula 2 to pass through holes 18 into the interior lumen 12. When cannula 2 is in position so that the distal tip 4 is in the inferior vena cava, the atrial basket 8 will be located in the center of the atrium. Consequently, blood entering the atrial basket through holes 18 will be blood in the right atrium from the superior and inferior vena cava. So, holes 18 drain blood from the right atrium into the cannula 2 and consequently into the extra-corporeal cardiac bypass system.

In the preferred embodiment, holes 18 are equally spaced around the outer circumference of cannula 2 at atrial basket 8. Further, in the preferred embodiment holes 18 are preferably elongated to allow greater flow area for the blood entering the cannula 2 through holes 18. Holes 18 are preferably elongated in the direction of elongation of cannula 2.

A reinforcing member 20 is integrally formed in the atrial basket 8 so that holes 18 pass through reinforcing member 20. A preferred embodiment of reinforcing member 20 is shown in detail in FIGS. 3, 4 and 5.

Figure 4B:
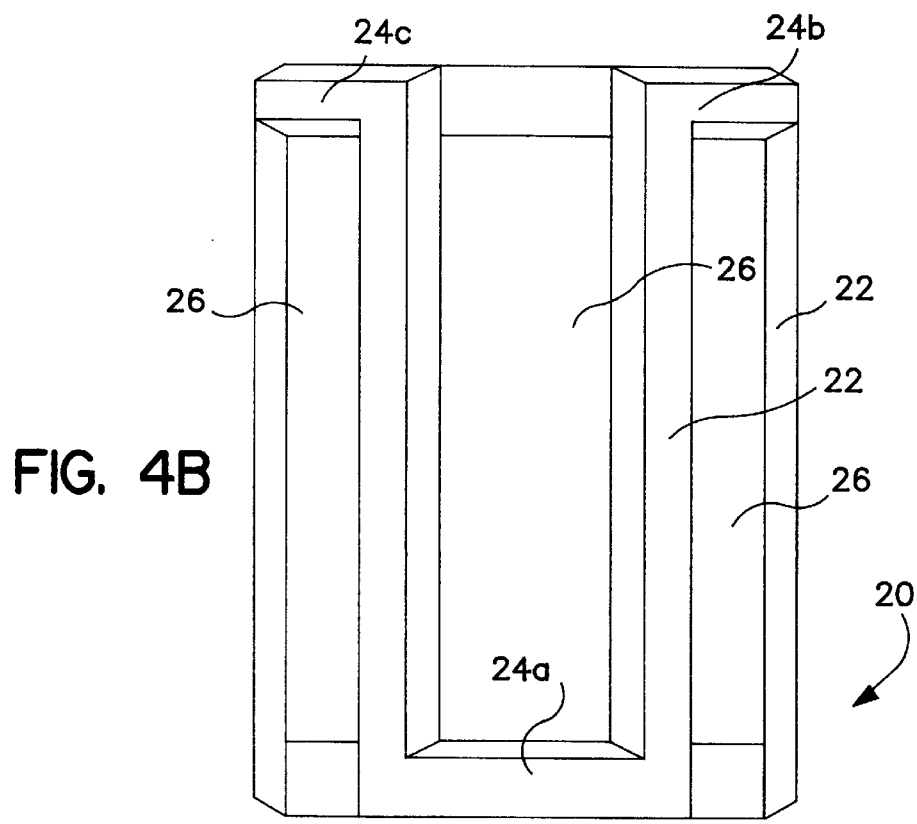

As can be seen in FIG. 4, reinforcing member 20 has an alternating series of parallel beams 22. Each beam 22 is connected to its neighbor beam 22 by a connecting piece 24. Each connecting piece 24 is attached to only two neighboring beams 22. Further, connecting pieces 24 alternately connect neighboring beams 22 at opposite ends of reinforcing member 20.

Figure 5A:
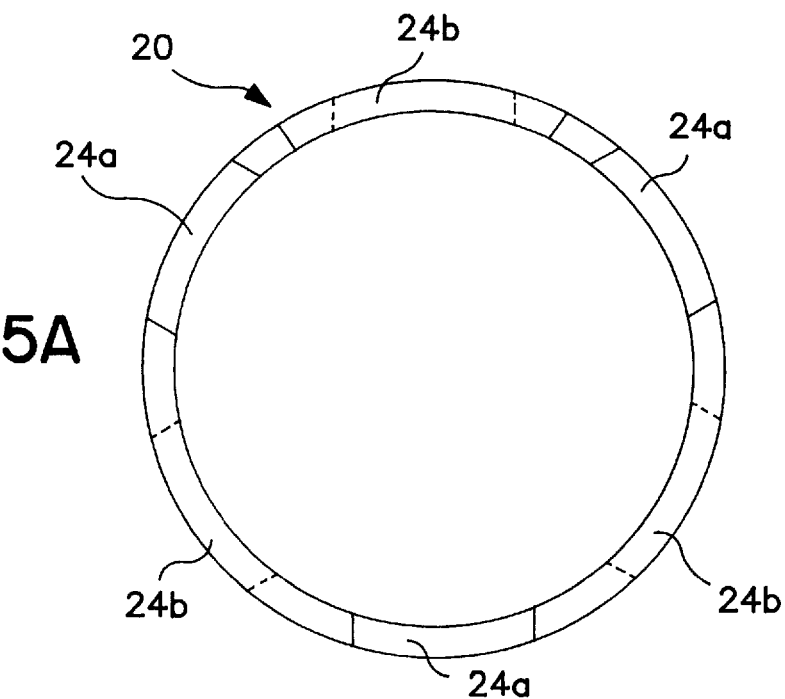
FIG. 5 is a top view of the reinforcing member of FIG. 4.
Figure 5B:
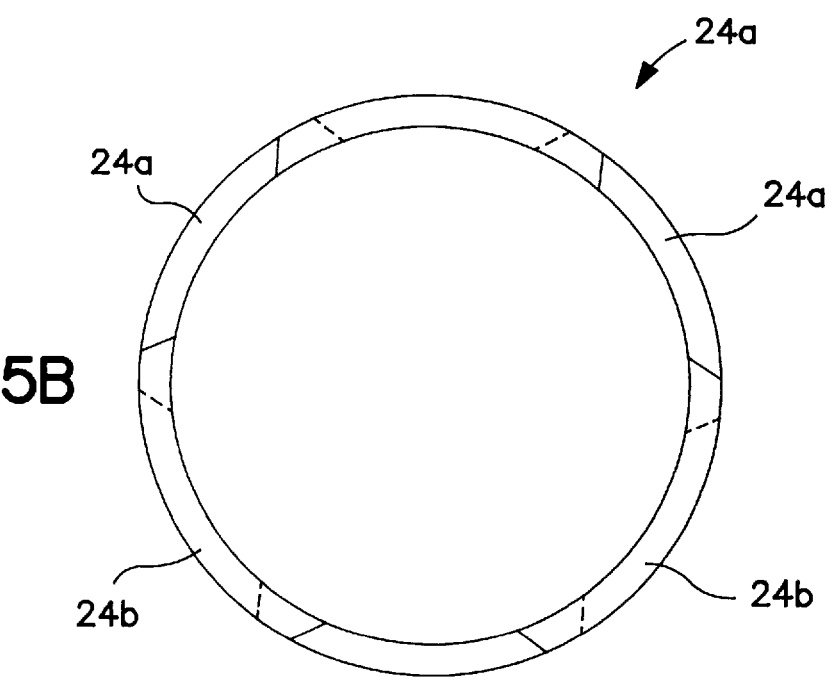

In FIGS. 4 and 5, connecting pieces on the distal end of reinforcing member 20 are labeled 24b while connecting pieces on the proximal end are labeled 24a. In this way, a continuous "path" is formed by following a beam 22 to a connecting piece 24a, to a neighboring beam 22, to a connecting piece 24b, to the next neighboring connecting piece 24a, to a connecting piece 24b and so on until returning to the starting point. Spaces 26 are formed between neighboring beams 22.

As can be seen in FIG. 5, reinforcing member 20 is preferably circular in cross-section with lumen 12 passing through the interior of reinforcing member 20 when in position at the atrial basket 8. Reinforcing member 20 is preferably integrally added to cannula 2 as described hereafter. In the preferred embodiment, there are six beams 22. In this preferred embodiment, there are then three each connecting pieces 24a and 24b.

In the preferred embodiment of cannula 2, a spring 28 or other means is added to cannula 2 in area D to make cannula 2 in area D more rigid and kink resistant. Spring 28, like spring 16, is preferably a helical wire having a diameter of about 0.015 inch. Spring 28 is preferably integrally formed in area D as will be described hereafter.

Although in the preferred embodiment the outer diameter of cannula 2 in area D includes a stiffening spring 28, this is not required to be so. It is within the scope of the invention that area D may be made more rigid and kink resistant by means other than spring 28. These means include, but are not limited to adding a stiffening layer to cannula 2 in area D and adding cross-linking agents to the plastisol that forms area D as will be described hereafter.

In an alternate embodiment of reinforcing member 20, a series of parallel beams 22 are formed as before. However, in this alternate embodiment, all connecting pieces 24 are located at the same end of reinforcing member 20. Connecting pieces 24 may be discrete or may be a single integral piece. In either embodiment, spaces 26 are formed having an open end opposite connecting pieces 24. In this alternate embodiment, an even or odd number of beams 22 may be provided extending away from connecting pieces 24.

Reinforcing member 20, shown in FIG. 4 and FIG. 5, is the preferred embodiment for reinforcing member 20. As can be seen, reinforcing member 20 in this preferred embodiment has six beams 22 and six corresponding connecting pieces 24. Although six beams 22 and six corresponding connecting pieces 24 is the preferred embodiment, the invention anticipates that other numbers of beams 22 and connecting pieces 24 can be used.

Figure 7:
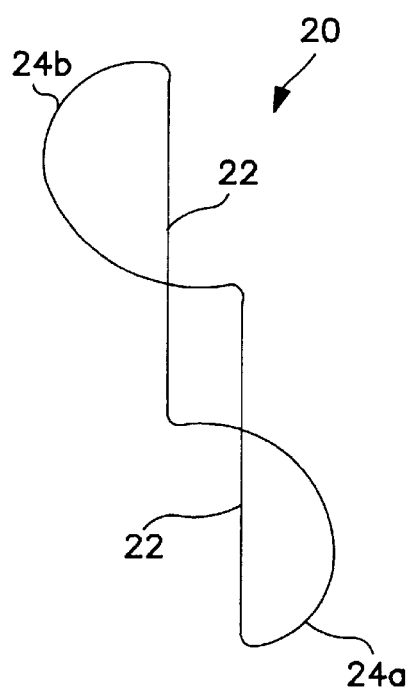
FIG. 7 is a perspective view of an alternate embodiment of the reinforcing member of FIG. 4.
Figure 8:
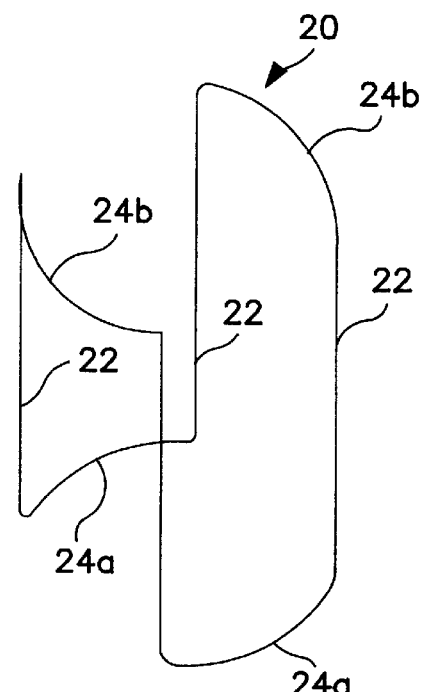
FIG. 8 is a perspective view of an alternate embodiment of the reinforcing member of FIG. 4.
Figure 9:
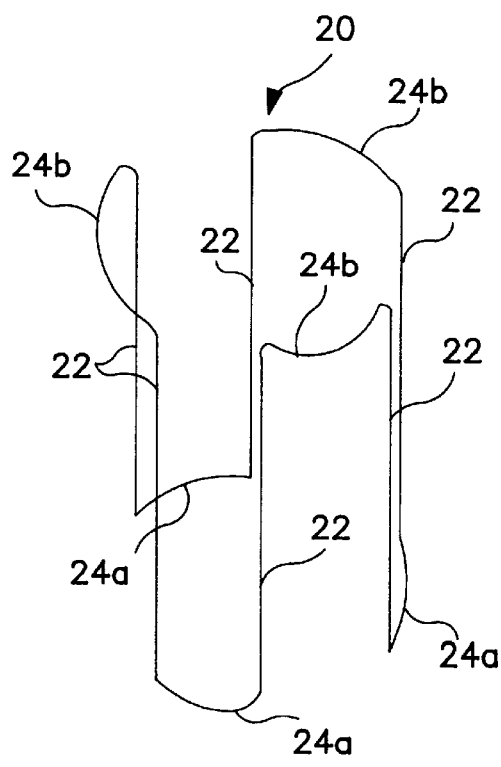
FIG. 9 is a perspective view of another alternate embodiment of the reinforcing member of FIG. 4.

Additional alternate embodiments of reinforcing member 20 are shown in FIGS. 7 through 9. The alternate embodiments of FIGS. 7 through 9 show reinforcing member 20 having two, four and eight beams 22 and corresponding connecting pieces 24, respectively. It is clear that additional numbers of beams 22 and connecting pieces 24 can be used as desired. In the preferred embodiment, an even number of beams 22 and connecting pieces 24 is required.

In the embodiment of FIG. 7, one connecting piece 24a and one connecting piece 24b is used. In the embodiment of FIG. 8, two connecting pieces 24a and two connecting pieces 24b are used. In the embodiment of FIG. 9, four connecting pieces 24a and four connecting pieces 24b are used. In all ways other than the number of beams 22, connecting pieces 24a and connecting pieces 24b, the reinforcing members 20 shown in FIGS. 7 through 9 are identical to the reinforcing member 20 of the preferred embodiment.

Reinforcing member 20 is preferably made of a material having the properties of being rigid and withstanding the curing temperature of plastisol without becoming soft and compliant. The reinforcing member must be rigid enough to prevent the cannula from kinking or collapsing during normal use. However, the reinforcing member should be flexible enough to accommodate variations in the individual molding pieces and variations encountered during the manufacturing process. Preferred materials include, but are not limited to, polyolefin materials and polyetherimide. Also preferred are rigid polyvinylchloride (PVC) materials that will fuse with the plastisol.

Figure 10:
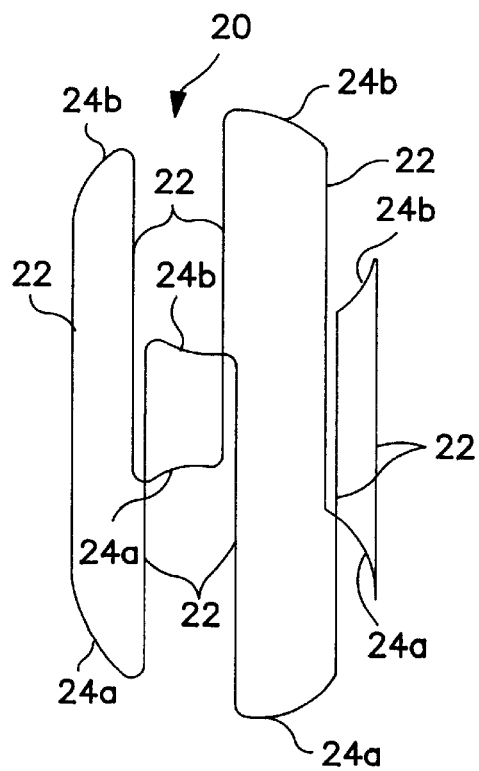
FIG. 10 is a perspective view of an alternate embodiment of the reinforcing member of FIG. 4.

FIG. 10 shows an alternate embodiment of the preferred embodiment and the embodiments of FIGS. 7 through 9. In this alternate embodiment, the material of reinforcing member 20 is a rigid metal wire. Reinforcing member 20 still has the beams 22 and connecting pieces 24a and 24b as before, but reinforcing member is formed by bending or molding the wire into the desired configuration of beams 22 and connecting pieces 24a,b.

As stated above, reinforcing member 20, in whatever embodiment, is preferably integrally formed in cannula 2. FIG. 6a through FIG. 6e show a preferred method for integrally forming reinforcing member 20 in cannula 2.

Figure 6A:
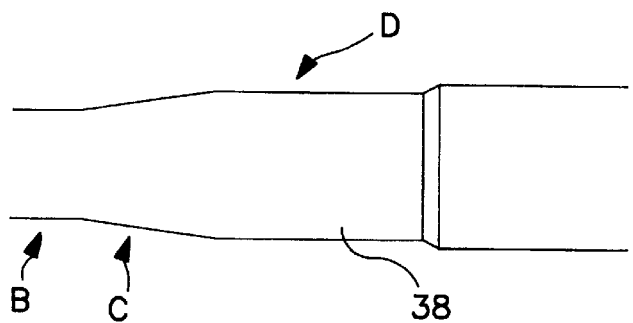
FIG. 6a–FIG. 6e are side elevational views showing the method of making the cannula according to FIG. 1.

FIG. 6a shows a metal mold 38 having an outer shape formed in the desired shape of the interior lumen 12. As can be seen, mold 38 has the shape that increases in outer diameter from distal end of 4 to the proximal end 6 of cannula 2 corresponding to the increasing outer diameters of areas A through D as described above.

Figure 6B:
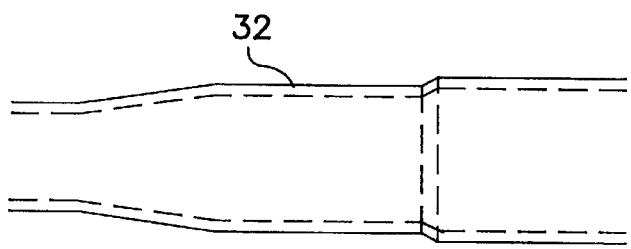

As shown in FIG. 6b, mold 38 is coated with a first layer of plastisol 40. This first layer of plastisol 40 is preferably deposited on metal mold 38 by dipping metal mold 38 in a vat of plastisol. The plastisol is preferably at room temperature. Thereafter, mold 38 is heated, as is well understood in the art, to set the plastisol.

Figure 6C:
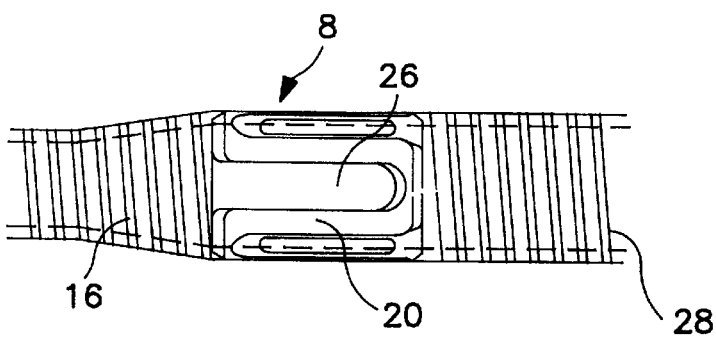

Reinforcing member 20 is placed over the first layer of plastisol 40 at the distal end of area D (FIG. 6c). Spring 16 is placed over the first layer of plastisol 40 at the proximal end of area B and over area C. Spring 16 extends proximally to approximately abut reinforcing member 20. Spring 28 is placed over the first layer of plastisol in areas D proximal to reinforcing member 20. Spring 28 extends proximally from the proximal end of reinforcing member 20.

Figure 6D:
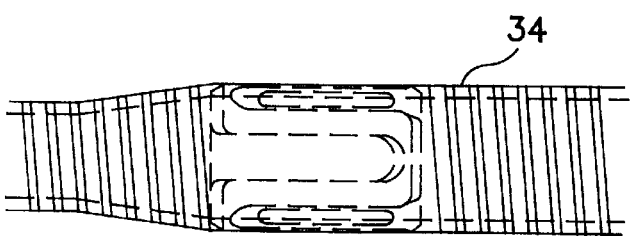

A second layer of plastisol 42 is applied to the cannula 2, thereby coating springs 16, 28 and reinforcing member 20 (FIG. 6d). The mold is heated again, as is well understood in the art, until both layers of plastisol 40, 42 are fully cured and fused together. Springs 16, 28 and reinforcing member 20 are thereby encapsulated in the wall of cannula 2. In the preferred embodiment, plastisol material, formed by both layers of plastisol 40, 42, is formed in spaces 26 between beams 22. In alternate embodiments, plastisol material, formed by both layers of plastisol 40, 42, is formed in holes 32 or holes 36.

Cannula 2 is removed from mold 38 by techniques which are understood in the art including but not limited to air assisted blow off.

Figure 6E:
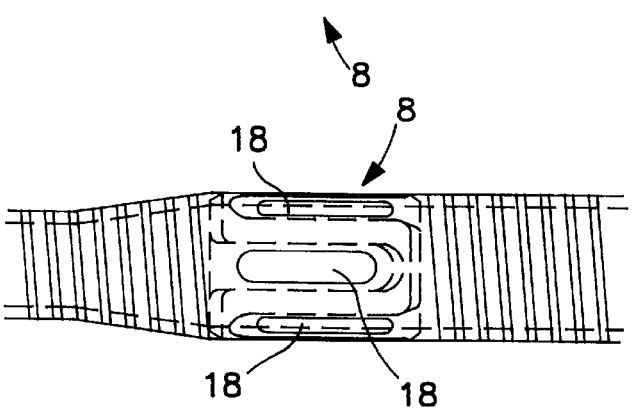

Holes 18 are punched through spaces 26 in reinforcing members 16 (FIG. 6e). In this way, holes 18 are formed through both layers of plastisol 40, 42 and allow blood access from the outside of cannula 2 to the interior lumen 12. The punches punching holes 18 in cannula 2 have only to punch through the layers of plastisol 40, 42 which are relatively more compliant than the relatively more rigid material of reinforcing member 20.

In the method described above, two layers of plastisol 40, 42 are applied to the cannula 2. However, it is possible to use only a single layer of plastisol, either 40 or 42, in the cannula. In the embodiment having only a first layer of plastisol 40, the method of forming a cannula 2 has the following steps. First, a mold 38 is provided having an outer shape formed in the desired shape of an interior lumen. The mold 38 is coated with a first layer of plastisol 40 and is then heated to set the first layer of plastisol 40. A reinforcing member 20 is placed over the first layer of plastisol 40 at a distance proximal to the distal end of the mold 38. The reinforcing member 20 preferably has at least one space 26 formed therethrough. The mold 38 is then reheated to fuse and embed the reinforcing member 38 in the plastisol. The cannula 2 is removed from the mold 38. A hole 18 is then punched through the first layer of plastisol 40 through the space 26 in the reinforcing member 20.

In the embodiment having only a single layer of plastisol that corresponds to the second layer of plastisol 42 in the preferred embodiment, the method of forming a cannula has the following steps. First, a mold 38 is provided having an outer shape formed in the desired shape of an interior lumen. A reinforcing member 20 is placed over the mold 38 at a distance proximal to the distal end of the mold 38. The reinforcing member 20 preferably has at least one space 26 formed therethrough. Mold 38 is coated with a layer of plastisol 42 to coat the mold 38 and the reinforcing member 20. Mold 38 is heated to set the layer of plastisol 42 over the mold 38 and the reinforcing member 20 and to bond and fuse reinforcing member 20 to the plastisol. The cannula 2 is removed from the mold 38. A hole 18 is then punched through the layer of plastisol 42 through the space 26 in the reinforcing member 20.

When practicing either of the embodiments having only a single layer of plastisol, all other elements, functions and methods are the same as is described above in connection with the preferred embodiment.

The invention has been shown and described in connection with specific embodiments. It is to be realized, however, that the description given herein is for the purpose of illustrating the invention and is not intended to be limiting. It is further understood that improvements and modifications to the disclosure made herein will occur to those skilled in the art and that such improvements and modifications will still fall within the scope of the invention.

I claim:

1. A two-staged venous cannula comprising:
   an elongated tubular body having a distal end and a proximal end and an interior lumen extending from the distal end to the proximal end of the body, the interior lumen being open at the proximal end of the body and being substantially enclosed at the distal end of the body, the body having at least one first hole near the distal end of the body extending from the outside of the distal end of the body to the interior lumen, the first hole providing fluid communication between the interior lumen and the exterior of the cannula at the distal end of the body; and,
   an atrial basket having a reinforcing member formed therewith, the atrial basket located proximal to the distal end of the body, the reinforcing member having at least one space through which at least one second hole passes to allow blood outside of the cannula to pass through the second hole into the interior lumen.

2. The cannula of claim 1 wherein the reinforcing member includes an alternating series of beams.

3. The cannula of claim 2 wherein at least two beams are parallel to each other.

4. The cannula of claim 2 wherein each beam is connected to its neighbor beam by a connecting piece.

5. The cannula of claim 4 wherein each connecting piece is attached to only two neighboring beams.

6. The cannula of claim 4 wherein at least one connecting piece connects neighboring beams at a first end of the reinforcing member and at least one connecting piece connects neighboring beams at a second end of the reinforcing member opposite the first end of the reinforcing member.

7. The cannula of claim 6 wherein each connecting piece alternately connects neighboring beams at opposite ends of the reinforcing member.

8. The cannula of claim 4 wherein at least two connecting pieces are located at the same end of the reinforcing member.

9. The cannula of claim 8 wherein each connecting piece is located at the same end of the reinforcing member.

10. The cannula of claim 2 wherein there are two beams.

11. The cannula of claim 2 wherein there are four beams.

12. The cannula of claim 2 wherein there are six beams.

13. The cannula of claim 2 wherein there are eight beams.

14. The cannula of claim 1 wherein the reinforcing member is made of a polyolefin.

15. The cannula of claim 1 wherein the reinforcing member is made of polyetherimide.

16. The cannula of claim 1 wherein the reinforcing member is made of PVC.

17. The cannula of claim 1 wherein the reinforcing member is made of metal.

18. The cannula of claim 1 wherein the reinforcing member is circular in cross-section.

19. The cannula of claim 1 wherein the reinforcing member is integrally formed in the cannula.

20. The cannula of claim 1 wherein the first holes are elongated.

21. The cannula of claim 20 wherein the elongated first holes have the axis of elongation aligned with lines that are parallel to the elongated axis of the body.

22. The cannula of claim 1 wherein the first holes are equally spaced around the outer of the cannula at the distal end of the body.

23. The cannula of claim 1 wherein the first holes are placed in several rows, each row spaced a different distance from the ultimate distal end of the body.

24. The cannula of claim 23 where in the first holes are located around the outer surface of the distal end of the body in rows so that the first holes in one row are offset the first holes in another row.

25. The cannula of claim 1 wherein the distal tip has a narrower outer diameter than the rest of the cannula.

26. The cannula of claim 1 wherein the distal tip of the cannula is rounded.

27. The cannula of claim 1 further comprising a first spring added to the cannula near the distal end of the body to make the distal end of the cannula more rigid and kink resistant.

28. The cannula of claim 27 wherein the first spring is a helical wire.

29. The cannula of claim 27 wherein the first spring is integrally formed in the cannula.

30. The cannula of claim 1 further comprising a stiffening layer added to the cannula near the distal end of the cannula to make the distal end of the cannula more rigid and kink resistant.

31. The cannula of claim 1 wherein the second holes are equally spaced around the outer circumference of the cannula at the atrial basket.

32. The cannula of claim 1 wherein the second holes are elongated.

33. The cannula of claim 32 wherein the second holes are elongated in the direction of elongation of the cannula.

34. The cannula of claim 1 further comprising a second spring added to the cannula proximal to the atrial basket to make the cannula proximal to the atrial basket more rigid and kink resistant.

35. The cannula of claim 34 wherein the second spring is a helical wire.

36. The cannula of claim 34 wherein the second spring is integrally formed in and extends proximally from the proximal end of the atrial basket.

37. The cannula of claim 1 further comprising a stiffening layer added to the cannula proximal to the atrial basket to make the cannula proximal to the atrial basket more rigid and kink resistant.

38. The cannula of claim 1 wherein the reinforcing member includes a molded cylindrical tube through which at least one space is formed, through which at least one second hole passes to allow blood outside of the cannula to pass through the second hole into the interior lumen.

* * * * *